United States Patent [19]

Lawton

[11] Patent Number: 4,495,291

[45] Date of Patent: Jan. 22, 1985

[54] INDICATORS FOR ETHYLENE OXIDE

[75] Inventor: William R. Lawton, Deerfield Beach, Fla.

[73] Assignee: Graphic Controls Corporation, Buffalo, N.Y.

[21] Appl. No.: 241,226

[22] Filed: Mar. 6, 1981

[51] Int. Cl.³ ............................................. G01N 21/78
[52] U.S. Cl. ........................................ 436/1; 422/57; 422/58; 427/2; 436/165
[58] Field of Search ........ 73/356; 23/232 R, 230 LC; 422/55, 56, 57, 58, 86, 87; 116/206, 207; 252/299.7; 436/1, 164, 165; 427/2

[56] References Cited

U.S. PATENT DOCUMENTS

| | | | |
|---|---|---|---|
| 2,998,306 | 8/1961 | Huyck et al. | 422/56 |
| 3,409,404 | 11/1968 | Fergason | 436/164 |
| 4,015,591 | 4/1977 | Suzuki et al. | 23/230 LC |
| 4,045,383 | 8/1977 | Koff | 23/230 LC |
| 4,271,121 | 6/1981 | Diller et al. | 422/57 |
| 4,285,697 | 8/1981 | Neary | 422/57 |

OTHER PUBLICATIONS

Brown, Glenn H., "Liquid Crystals", *Industrial Research*, May 1966, pp. 53-58.

Primary Examiner—Arnold Turk
Attorney, Agent, or Firm—Michael G. Berkman

[57] ABSTRACT

A device for giving a visual indication of the amount of residual ethylene oxide present in ethylene oxide treated solid hospital articles and other health devices. The amount of residual ethylene oxide is indicated by the difference in color exhibited by different sensitized areas of the device in the form of an opaque dark colored support member having bonded to its surface a thin film of a cholesteric liquid crystal composition in a solid film-forming binder. The film is made by laying down on the surface of the support member a solution or dispersion of liquid crystals which exhibits a change in color when in contact with ethylene oxide at a temperature from 60° to 100° F. in a solution of the solid binder, then evaporating the solvent. As prepared, the film is in a form adapted to be packaged with goods to be subjected to sterilization with ethylene oxide, a portion of the film being sealed within a transparent enclosure the walls of which possess a permeability to ethylene oxide no greater than that of the material of the treated goods.

9 Claims, 4 Drawing Figures

INDICATORS FOR ETHYLENE OXIDE

BACKGROUND OF THE INVENTION

This invention relates to novel indicator devices for determining the amount of ethylene oxide absorbed during the ethylene oxide sterilization of hospital supplies and related health care materials. The invention is useful in determining when a level of ethylene oxide is reached, upon aeration, which is no longer a health hazard should the sterilization items come into contact with the human body.

Items sterilized with ethylene oxide biocidal gas must be properly aerated so that the release of residual gas during use of the treated item will not cause hemolysis, erythema, and edema of the tissues, or otherwise harm the body. It is estimated that more than 10,000 ethylene oxide sterilization units are installed in U.S. hospitals. Such sterilizers are normally operated at 50°–60° C. and steam is introduced during the biocidal or sterilization cycle to provide the humidity required for the process. This processing results in the breakdown of some of the ethylene oxide to give ethylene glycol and 2-chloroethanol. The latter may be formed during ethylene oxide sterilization when there is a source of chloride as in polyvinyl chloride. Water may react with ethylene oxide to produce ethylene glycol during sterilization.

The Federal Register Vol. 43, No. 122, p. 27482 contains rules (proposed by the Department of Health, Education, and Welfare) that devices contacting blood or large implants shall not contain more than 25 parts per million of ethylene oxide and devices contacting skin shall not contain more than 250 parts per million of ethylene oxide. The laboratory analysis for ethylene oxide is complex, expensive, and time consuming. Therefore, hospitals have relied on aerating for excessively long periods of time to ensure having reached a safe level of residual ethylene oxide biocidal gas. Resulting time delays cause shortages of available materials for hospital operations. excessive stockpiling of hospital items, and often the unknowing use of sterilized items which contain concentrations of ethylene oxide hazardous to health. There exist indicator strips or tags which undergo a permanent color change on exposure to ethylene oxide. These, however, do not show the amount of effective exposure of the items being sterilized. No simple indicators are available which attest to the adequacy of the items being sterilized. No simple indicators are available which attest to the adequacy of ethylene oxide exposure or which give the residual ethylene oxide remaining after exposure. The Canadian Government has recognized an urgent need for the type of device described in this invention and has granted approximately 250 thousand dollars to support the development of the product of this invention.

THE STATE OF THE ART

Liquid crystals and their properties are well known and the many technical articles including review articles published provide general information on liquid crystals and their properties. See for example G. H. Brown and W. G. Shaw, Chemical Reviews, Vol. 57, No. 6, December 1957, p. 1,049 titled "The Mesomorphic State -Liquid Crystals", Glenn H. Brown, Analytical Chemistry Vol. 41, No. 13, November 1969, p. 26A titled "Liquid Crystals and Some of Their Applications in Chemistry" and L. Melamed and D. Rubin, Applied Optics, Vol. 10, No. 5, May 1971 p. 1103 titled "Selected Optical Properties of Mixtures of Cholesteric Liquid Crystals".

Liquid crystalline materials have properties intermediate between those of a true liquid and a true crystal, having both an ordered structure and fluidity. The structure of cholesteric materials is markedly different from that of other liquid crystal structures. The differences of the cholesteric structure include optical negativity compared with optical positivity of the other structures. The cholesteric structure is optically active and shows a strong optical rotatory power, and the cholesteric phase scatters white light selectively to give vivid colors. The cholesteric phase can selectively rotate circularly polarized light either clockwise or counterclockwise and the mean wave length of the reflection band from the cholesteric phase depends upon the angle of incidence of the beam.

The detection of gases and other impurities by cholesteric liquid crystals has been reported in the above references and in others. Fergason, U.S. Pat. No. 3,409,404 describes the use of cholesteric liquid crystals to identify unknown gases and other materials. No reference is made in published literature to the identification of the quantity of ethylene oxide present in a material or as to the use of cholesteric liquid crystals in an indicator system for ethylene oxide sterilization, despite the urgent need for such an indicator as a means for insuring against health hazards caused by exposure to ethylene oxide. The technology as known will not of and by itself provide the functions of the indicator device described in this invention. No prior art indicator is operable over the wide range of temperatures normally encountered in the hospitals.

Fergason clearly states that the cholesteric liquid crystals of his invention are temperature sensitive and that analyses must be conducted at a known calibrated temperature. Such temperature dependency is a recognized characteristic of liquid crystals. A second well known property of cholesteric liquid crystals is the dependence of color response on the purity of liquid crystal or of a mixture of liquid crystals being used. Purification of the liquid crystals is both difficult and expensive. It is an important feature of the present invention that a high degree of chemical purity is not required for proper practice of this invention. Cholesteric liquid crystals deteriorate on exposure to light, oxidation, and through contact with atmospheric impurities on aging. Such deterioration changes the response to temperature and to exposure to the agents which are being analyzed or assayed. Dixon et al. U.S. Pat. No. 3,656,909 recognized these instabilities as a disadvantage of the above cited Fergason teaching and attempted to minimize the problem by addition of UV radiation stabilizers consisting of aromatic azo or aromatic azoxy compounds.

The effect of aging is minimized in the indicator of the present invention. The degradation products obtained during the sterilization cycle with ethylene oxide, e.g. ethylene glycol will remain after aeration, and act to change the color response of the liquid crystal systems known in the art. The present invention compensates for the residual non-volatile materials remaining after aeration. A color blind person could not distinguish the color changes occuring in the cholesteric liquid crystal systems of the prior art. In contrast, a person does not have to perceive color to use the indicator article of the present invention.

SUMMARY OF THE INVENTION

The present invention provides a practical, highly effective, inexpensive and sensitive ethylene oxide indicating device which may be incorporated into a package along with hospital or surgical goods to be sterilized by ethylene oxide treatment. Upon exposure of the treated article to aeration, by user, to eliminate retained or absorbed ethylene oxide before use on the body, the device of the invention provides a rapid and sensitive indication of the effectiveness of the aeration. Specifically, the device undergoes a change in reflective color so that the exposed control and test areas of the device can be compared to determine when the amount of residual ethylene oxide in the sterilized items has reached a safe reduced level.

In accordance with the invention the sensitized layer in the control and test areas is a cholesteric liquid crystal coating. No manipulation of the indicator device is required and no technical skill is needed for its use. Since the test area and the control go through the same aging processes, the same exposure to light, and the same retention of the ethylene glycol and other degradation products of ethylene oxide during the sterilization cycles, the results or effects of these factors or variables are compensated. Thus, the differential in color between the test and control areas is a representation of the concentration of ethylene oxide in the test area. Since the sensitized layer consisting of cholesteric liquid crystals is the same in the control and test areas, the liquid crystals do not have to be extremely pure to have the color differentials representative of the amount of retained ethylene oxide in the test section. During the aeration process, the control area loses its ethylene oxide rapidly to reach a near zero level of ethylene oxide while the test area representing the sterilized item will lose its ethylene oxide content at approximately the same rate as the sterilized item. The same device may be used to indicate the amount of ethylene oxide absorbed during the sterilization process. In this case, the control area will rapidly reach saturation with ethylene oxide and the color formed compared to the test area will show how much ethylene oxide has been absorbed by the item being sterilized.

DESCRIPTION OF PREFERRED EMBODIMENTS

One embodiment of the invention comprises an opaque dark-colored support member having on its surface a thin coating or film consisting essentially of a cholesteric liquid crystal composition exhibiting a color change in reflective light when exposed to ethylene oxide at a temperature from 60° to 100° F, the liquid crystals being dispersed in a solid non-tacky film-forming binder. The coating or film is formed by applying to the surface of the support member a solution of the binder in a liquid solvent. The solution also contains the desired liquid crystal composition which can be either dispersed in the form of small droplets as the inner or disperse phase of a two-phase system, or dissolved in the solvent along with the binder to form a single phase system. The solvent is then evaporated to provide a solid coating of film bonded to the support member and in the form of a single or two-phase system corresponding to the phases of the liquid coating composition.

In one preferred embodiment a portion of the coating or film is sealed within an enclosure formed of plasticized polyvinyl chloride. Most hospital and surgical goods packaged for sterilization with ethylene oxide constitute textile fabrics, rubber or various synthetic plastics compositions. It has been found that of all these materials usually present in such packages, items made of plasticized polyvinyl chloride retain ethylene oxide most tenaciously. By providing a portion of the indicator coating or film sealed within an enclosure, the walls of which possess a permeability to ethylene oxide no greater than that of plasticized polyvinyl chloride, or in any event, no greater than that of whatever goods are present in the package, and by providing another portion of the coating or film in the indicator device which is exposed to the atmosphere and from which residual ethylene oxide is consequently eliminated very rapidly upon aeration, the indicator makes possible a direct color comparison of two adjacent zones of the same coating. This technique automatically eliminates possible errors caused by temperature differences between the indicator coating or film and a color standard used for comparison, any effect of residual ethylene glycol due to degradation of ethylene oxide, any differences in aging between film in the indicator and in the color standard. Also minimized is the need for close quality control of separate coatings made from different batches of liquid crystals.

The support member may be any solid material either rigid or flexible which does not react chemically with the liquid crystal so as to interfere with its optical capabilities. The support member also must allow permeation of ethylene oxide at a rate equal to or faster than the enclosure material. Substrates with devices using polyvinyl chloride as the enclosure material may be, for example, unplasticized polyvinyl chloride, cardboard, polyethylene, polypropylene, etc., but not impervious materials such as glass, metals, or ceramics. It is preferred to use support members which are as thin as possible while still providing the requisite strength.

The cholesteric liquid crystal composition employed can be any such material or mixture of materials which provides a visual indication, i.e., a reversible change in color by reflective light when exposed to ethylene oxide. For best results, that is, for readily observable color changes throughout a temperature range, from 60° to 100° F., it is preferred to employ a mixture of three different types of cholesteric liquid crystals. The mixture includes 30% to 80% by weight of a cholesteryl ester of a fatty acid having from 6 to 20 carbon atoms, from 5% to 40% of a member selected from the group consisting of cholesteryl oleyl carbonate and cholesteryl 2-(2-alkoxyethoxy) ethyl carbonates in which the alkoxy group has from 1 to 4 carbon atoms, and from 0.5% to 40% of a member selected from the group consisting of cholesteryl benzoate, cholesteryl cinnamate, cholesteryl furfuryl carbonate, cholesteryl allyl carbonate, cholesteryl bromide, cholesteryl nitrate, cholesteryl cinnamyl carbonate, and cholesteryl methallyl carbonate. In other compositions, a mixture containing two or more components from the same "group" may be used.

The minimum amount and maximum amount of each of the three types used varies depending upon the identity of the member of each type which is used and can readily be determined by simple experiments. In general, the proportions of each lie within the limits set forth above.

Among cholesteryl esters of fatty acids which can be used are cholesteryl hexamoate, cholesteryl octanoate, cholesteryl nonanoate, cholesteryl decanoate, cholesteryl dodecanoate, cholesteryl laurate, cholesteryl myristate, cholesteryl palmitate and cholesteryl oleate; of these the nonanoate is preferred for convenience and commercial availability. The mixed carbonate esters of the second type include cholesteryl 2-(2-methoxyethoxy) ethyl carbonate, cholesteryl 2-(2-ethoxyethoxy) ethyl carbonate, 2-(2 propoxyethoxy) ethyl carbonate and cholesteryl 2-(2-butoxyethoxy) ethyl carbonate.

The binder can be any non-tacky film-forming solid material preferably an organic polymer, which does not react chemically with the cholesteric liquid crystal and does not interfere with its sensitivity to ethylene oxide and which is soluble in a solvent which can be removed by evaporation at a temperature at which the binder and cholesteric liquid crystals are not substantially degraded or decomposed, i.e., at a temperature up to about 250° F. The binder serves to protect the liquid crystal from air oxidation, modifies the sensitivity range of the liquid crystal mixture and also provides durability by preventing smearing or removal of the liquid crystal material if it is accidentally brought into contact with another surface.

The solvent is any liquid capable of dissolving the selected binder to form a solution containing at least 20% by weight of binder and which does not react chemically with the binder or with the liquid crystal. In the preferred embodiment, the solvent is also capable of dissolving the cholesteric liquid crystal to form a solution containing at least 10% by weight of liquid crystal, in which case the mixed solution is in the form of a single phase system or lacquer.

A suitable binder is any of a wide variety of synthetic plastic materials including polyvinyl acetate, acetal homopolymers and copolymers, cellulose esters such as cellulose acetate or butyrate, polyester resins, acrylic resins including polymers and copolymers of acrylic and methacrylic esters, styrene polymers and copolymers, and the like. A variety of readily available liquid organic solvents boiling at temperatures up to 250° F. can be used for the foregoing binders to form single-phase systems. Typical solvents include any of the commonly used alcohols, ketones, esters, or hydrocarbons, either aromatic or aliphatic, most of which readily dissolve the cholesteric liquid crystal. Evaporation of the solvent from such solutions leads to the formation of a solid single phase system, i.e., a solution dispersion.

It is also possible to employ, for certain binders, a liquid solvent which is incapable of dissolving the cholesteric liquid crystal, in which case the liquid crystal is dispersed in the solution of binder to form a two-phase system or dispersion in which the binder is in the continuous phase and the liquid crystal is in the dispersed or inner phase. The most convenient and satisfactory solvent for forming such two-phase systems is water. One may use with the water solvent a variety of film forming non-tacky water-soluble binders such as polyvinyl alcohol, polyvinyl pyrrolidone, gelatin, starch, casein, polyacrylic acid, and copolymers of styrene or ethylene with maleic anhydride which can be dissolved in water with the aid of ammonia. Evaporation of water from such two-phase systems leads to the formation of a solid two-phase system in which the droplets of liquid crystal are dispersed throughout the mass of solid binder.

An alternative two-phase system may be prepared by dispersing microcapsules of liquid crystals obtained by common processes well known in the art in either a water or solvent base solution of the previously mentioned binders and forming a film which upon drying contains the microcapsules as one phase dispersed in a dry film of the binder as the second.

The ratio of cholesteric liquid crystal to binder can vary from 1:10 to 1:1 by weight, although a ratio in the range from 1:4 to 1:2 by weight is generally preferred. It has been found that in the case of both systems, the color intensity of the coating or film increases in proportion to the amount of liquid crystal present. It has also been found, surprisingly and quite unexpectedly, that the color change temperature range is higher for single-phase systems than for two-phase systems, offering the advantage that coatings or films which are single-phase systems are less affected by temperature fluctuation within the 60° to 100° F. range normally encountered during aeration of the package. Coatings or films having the single-phase system are more uniform, smoother and harder than are the coatings or films having two-phase systems. The increase in color response temperature range for single-phase systems over two-phase systems (as well as over the pure liquid crystal without binder) indicates the interaction between binder and liquid crystal, the precise extent of which depends upon the identity of the specific binder employed.

The amount of solvent used is not critical; it is desired of course, that the solution be sufficiently fluid so that it can readily be formed into a coating or film on the support member. It is undesirable, however, to use excessively large quantities of solvent because of increased cost and extended drying times during processing. When the solvent is incapable of dissolving the cholesteric liquid crystal, it is preferred to form a dispersion of the liquid crystal in a solution of the binder without the aid of wetting or dispersing agents, these tending to interfere with the properties and characteristics of the liquid crystal. It is preferable to rely simply upon mechanical dispersion or stirring of the ingredients. In general, it is desirable that the solution should contain at least 10% by weight of binders; solutions containing larger concentration up to 50% by weight or even more may also be used.

In manufacturing the indicators of the present invention, the solution or dispersion of liquid crystal in binder solution is simply layed down on the surface of the support member to form a coating or film. Then the solvent is evaporated either at room temperature or at elevated temperatures up to 250° F. to form a solid coating or film bonded to the support member. The solid film or coating thus formed can vary greatly in thickness although a thickness of at least 0.3 mil is usually desired to ensure sufficiently conspicuous color changes upon exposure to ethylene oxide in order to provide an indicator of the desired sensitivity when observed by the naked eye.

BRIEF DESCRIPTION OF THE DRAWINGS

In the appended drawings

Figures 1, 2, 3:
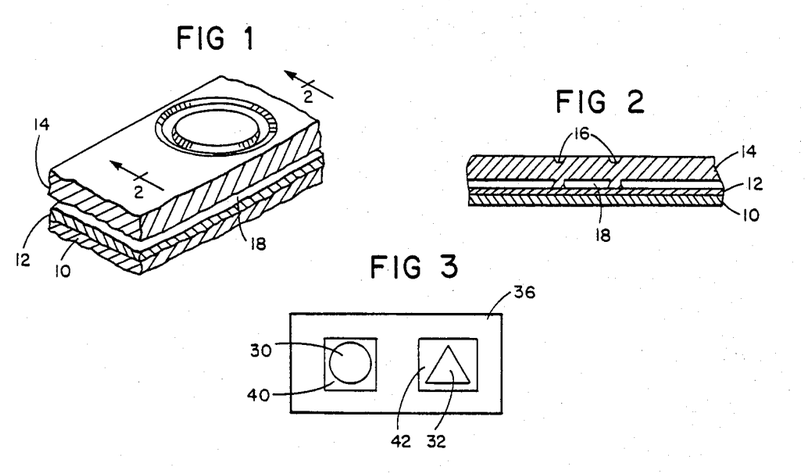
FIG. 1 is a perspective, enlarged view of a preferred embodiment of the invention showing the components thereof.
FIG. 2 is a cross-sectional view taken along lines 2—2 of FIG. 1.
FIG. 3 illustrates an embodiment of the visual indicator of the invention, which is meaningfully readable even by a color blind person.

In the drawing, there is shown for illustrative purposes, an indicator comprising a support member 10 in the form of a flexible support sheet or film of unplasticized high molecular weight polyvinyl chloride approximately 3 mils thick. Carbon black pigment is dispersed in the film to render it opaque and black. Such a support member allows ethylene oxide to diffuse rapidly through any overlying film both during the sterilization and the aeration processes. On the upper face of the support member 10 is a solid intermediate coating or film 12 preferably in a range from 0.3 to 1.5 mils thick formed by applying to the surface of the support sheet 10 a composition consisting of a cholesteric liquid crystal material in a solution of a normally solid binder, and then evaporating the solvent. The evaporation is conveniently carried out by allowing the coating to dry overnight at room temperature, and then heating the coated sheet 10 for two hours at 200° F.

Superimposed on the surface of the coating 12 is a 9 mil thick, high molecular weight polyvinyl chloride cover sheet 14 plasticized with dioctylphthalate a plasticizer commonly employed in hospital and surgical goods made of polyvinyl chloride. Conveniently, the thickness of the cover sheet 14 is chosen to correspond, for example, to the wall thickness of commercially used polyvinyl chloride tubing. The sheet thickness may be varied to match or to correlate with the bulk or thickness of the hospital articles or supplies being tested, if desired. The composite assembly is heat sealed in an annular path 16 to define a central zone 18 of film 12 hermetically enclosed within and visible through the cover sheet 14. Both the exposed marginal area 14a of sheet 14 and the sealed zone 18 are identical in composition, color and appearance.

In use, the indicator of the invention is placed within a package along with the products to be sterilized and exposed to a mixture of ethylene oxide and freon for example (12:88), conventionally used for sterilization purposes. During this period, both the exposed area of coating or film 12 and the sealed zone 18 change in color as viewed in reflected white light. The difference in color between film 12 and the sealed portion 18 indicates the amount of ethylene oxide absorbed by the plasticized polyvinyl chloride cover sheet 14 which directly corresponds to that absorbed by the articles of polyvinyl chloride being sterilized.

When the treated package is to be used, it is allowed to aerate either at ambient conditions or at room temperature or elevated temperatures c. 125° F. in an atmosphere of circulating forced air. The exposed area of coating or film 12 changes back to its original color after a few minutes exposure to the atmosphere if the liquid crystal film has a sensitivity to ethylene oxide at only relatively high concentrations (c. 250+parts/ million). When the color of the sealed zone 18 matches that of the exposed area of coating 12, the plasticized polyvinyl chloride sheet 14 and the items in the package have reached the minimum concentration of absorbed ethylene oxide, within the limits of sensitivity of the liquid crystal film coating 12. Liquid crystal films 12 of higher sensitivity eg. 25 parts/million very often will not return to the original color, presumably due to the presence of degradation products, such as ethylene glycol, formed during the sterilization and aeration processes. In such cases, the concentration of ethylene oxide in the plasticized polyvinyl chloride sheet 14 and the polyvinyl chloride items being aerated have reached the level of the minimum sensitivity of the liquid crystal film 12, c. 25 parts/million when the sealed test zone 18 reaches the same color as liquid crystal film 12. Liquid crystal film 12 may have a sensitivity to amounts of ethylene oxide less than 25 parts/million. In this case, the safety level of 25 parts/million is indicated by the difference in color between liquid crystal film 12 and the sealed zone 18.

In preparing the coating solution to be applied to the support member 10 in the case of the single phase system, the components making up the liquid crystal formulation are weighed out, then thoroughly mixed in the molten state and added hot to the binder solution. The resulting mixture is stirred until it becomes homogeneous. Some solutions are perfectly clear while others develop a haze or cloudiness. The mixed solution is applied to a support, e.g. black unplasticized 3 mil polyvinyl chloride by conventional draw-down techniques, the thickness of the coating to be applied being selected to provide the desired thickness of the final dried coating or film after evaporation of the solvent. The coating is allowed to dry by exposure to air at ambient temperature.

In the case of a two-phase system, the components of the liquid crystal formulation, after weighing, are melted and stirred to form a clear mixture or melt at a temperature of about 200° to 250° F. The hot melt is added dropwise to a water solution of the binder maintained at a temperature of 180° to 200° F. with high speed stirring to ensure the formation of a uniform, fine-particle emulsion. The emulsion is allowed to cool, and any foam is removed from the surface. The cooled emulsion is applied by conventional draw-down procedures onto a support member as described above, and then dried by exposure to air at room temperature.

After drying for several hours at room temperature, the coated sheet is heated in an oven at 200° F. for two hours to ensure complete removal of solvent. The dry sheet is cut into pieces of appropriate size, about one inch by three inches. A piece of one-inch square, 9 mil thick clear, transparent polyvinyl chloride plasticized with dioctylphthalate or equivalent plasticizer is then heat sealed to the coated side of the support member by means of a heated iron or platen.

In evaluating the indicators by exposing them to ethylene oxide and then aerating, standard samples of polyvinyl chloride plasticized with dioctylphtalate in the form of 9 mil film are exposed and aerated along with the indicator articles, under the same conditions. Changes in colors of the indicators are recorded at intervals during exposure and aeration. At the same time, samples of the standard film are removed and assayed for ethylene oxide by gas chromatography. By this procedure it has been demonstrated that indicators of the present invention are capable of indicating by color change the presence of as little as 25 parts/million or less of residual ethylene oxide in the film.

The following tabulations give examples of various liquid crystal mixtures in terms of parts by weight useful in the present invention.

EXAMPLE 1

55.47 cholesteryl nonanoate
14.93 cholesteryl benzoate
24.60 cholesteryl oleyl carbonate
5.00 cholesteryl 2-(2-ethoxyethoxy) ethyl carbonate

EXAMPLE 2

55.47 cholesteryl nonanoate
14.93 cholesteryl benzoate
24.60 cholesteryl oleyl carbonate
5.00 cholesteryl 2-(2-butoxyethoxy) ethyl carbonate

EXAMPLE 3

55.47 cholesteryl nonanoate
14.93 cholesteryl benzoate
24.60 cholesteryl oleyl carbonate
5.00 cholesteryl 2-(2-methoxyethoxy) ethyl carbonate

EXAMPLE 4

61.3 cholesteryl nonanoate
17.6 cholesteryl benzoate
21.1 cholesteryl cinnamyl carbonate

EXAMPLE 5

55.47 cholesteryl nonanoate
14.93 cholesteryl benzoate
24.60 cholesteryl oleyl carbonate
5.00 cholesteryl methallyl carbonate

EXAMPLE 6

55.12 cholesteryl nonanoate
14.56 cholesteryl benzoate
29.52 cholesteryl oleyl carbonate
0.80 cholesteryl furfuryl carbonate

EXAMPLE 7

52.75 cholesteryl nonanoate
29.75 cholesteryl oleyl carbonate
17.50 cholesteryl benzoate

EXAMPLE 8

57.62 cholesteryl nonanoate
32.38 cholesteryl oleyl carbonate
10.0 cholesteryl benzoate The liquid crystal formulations of Examples 1–6 were mixed with a resin lacquer solution to form a single phase system, as described above, the ratio of liquid crystal to resin being in each case 1:4 by weight. The liquid crystals of Examples 7 and 8 were dispersed in an aqueous solution of polyvinyl alcohol (6% by weight) sold under the trade name ELVANOL 52-22 to form a two-phase system as described above, the weight ratio of liquid crystal to polyvinyl alcohol being 1:4. The following tabulation summarizes the coating solutions or dispersions thus prepared.

Tabulation

| Binder Solution | Liquid Crystal Formulation |
| --- | --- |
| (a) DeSoto E 310 | Ex. 1,2,5,6 |
| (b) Monsanto 264 | Ex. 1,2,3,5,6 |
| (c) Bakelite Acrylic 203 | Ex. 1,3,4,5,6 |
| (d) DeSoto E 308 | Ex. 2,6 |
| (e) Ashland EP-8911-7-7 | Ex. 2,4,6 |
| (f) Stein-Hall 1560 | Ex. 2,3,5,6 |
| (g) Acryloid P-66 (50%) | Ex. 6 |
| (h) DeSoto E 306 | Ex. 6 |
| (i) National Starch 3392 | Ex. 6 |
| (j) Reichhold ESL-2294 | Ex. 6 |
| (k) Reichhold ESL-2308 | Ex. 6 |
| (l) Aqueous solution 6% of ELVANOL 52-22 | Ex. 7,8 |

The foregoing liquid solutions or dispersions were applied to a support member as described above and made up into indicators as shown in FIG. 1. In each case, in the absence of ethylene oxide, a characteristic initial color of the indicator by reflected white light is obtained at any given temperature in the range from 60° to 100° F., and in each case, the indicator displayed a distinctive change in color in the presence of small quantities of ethylene oxide. The initial color and the color in the presence of ethylene oxide occuring at room temperature (72° F.) are shown in Table 1:

TABLE 1

| Liquid Crystal Formulation and Binder | Initial Color | Color Induced by Ethylene Oxide |
| --- | --- | --- |
| Ex. 1 | | |
| a | Ochre-brown | Blue→black |
| b | Rose-brown | Purple |
| c | Red-blue-green | Purple |
| Ex. 2 | | |
| b | Black | Blue→purple |
| d | Yellow-brown | Green→red→purple |
| e | Blue | Purple→black |
| f | Black | Red→blue→purple |
| Ex. 3 | | |
| a | Green | Blue→purple→green |
| b | Rose | Blue→purple |
| c | Red-green | Blue→purple |
| f | Blue-green | Purple→black |
| Ex. 4 | | |
| c | Black | Brown→green→blue |
| e | Black | Blue→green |
| Ex. 5 | | |
| a | Green | Blue→black |
| b | Brown-green | Blue→purple |
| c | Green | Purple |
| f | Yellow-green | Purple |
| Ex. 6 | | |
| a | Black | Red→purple |
| b | Black | Green→purple |
| c | Black | Blue→purple |
| d | Black | Red→blue |
| e | Black | Red→green→purple |
| f | Black | Blue→purple |
| g | Black | Red→green |
| h | Black | Blue→purple |
| i | Black | Blue→purple |
| j | Black | Blue→purple |
| k | Black | Blue→purple |
| Ex. 7 | | |
| l | Red | Blue→purple |
| Ex. 8 | | |
| l | Black | Green→Blue→purple |

In many cases the color of the indicator undergoes a series of changes with increasing exposure or loss of ethylene oxide and in some cases the final color after aeration to remove ethylene oxide is not identical to the original color, although usually close to it.

| Formula | Indicating level of ETO |
| --- | --- |
| Ex. 1 | |
| (b) | ~400 ppm (48 hrs.) |
| (d) | ~400 ppm (48 hrs.) |
| (i) | ~280 ppm (144 hrs.) |
| Ex. 2 | |
| (d) | ~400 ppm (48 hrs.) |
| (h) | ~360 ppm (72 hrs.) |
| Ex. 3 | |
| (a) | <280 ppm (over 144 hrs.) |
| (c) | <280 ppm (over 144 hrs.) |
| (e) | ~400 ppm (48 hrs.) |
| (g) | ~280 ppm (144 hrs.) |
| (i) | ~400 ppm (48 hrs.) |
| Ex. 4 | |
| (c) | ~440 ppm (168 hrs.) |
| (e) | ~1040 ppm (24 hrs.) |

-continued

| Formula | Indicating level of ETO |
|---|---|
| Ex. 5 | |
| (b) | ~360 ppm (216 hrs.) |
| (f) | ~380 ppm (192 hrs.) |
| Ex. 6 | |
| (e) | ~480 ppm (96 hrs.) |
| (f) | ~480 ppm (96 hrs.) |

These examples show the selection of particular liquid crystal compositions in combination with different binders can be used to provide desired sensitivity levels of ethylene oxide and color play temperature ranges.

Table 2 shows the temperature color play range of the examples. In some cases Ex. 1 a, b, Ex. 2 d, Ex. 3 a, c,e,g, i, Ex. 4 c, and Example 5 b, f, the liquid crystal coatings exhibit colors at temperatures below room temperature (72° F.). The remainder are black at room temperature and do not show colors until warmed above 72° F. Table 2 shows that a broad range of color play temperatures is possible, from which the investigator may choose the conditions which fit desired conditions.

Table 3 shows the response of the various indicator examples to different exposure times to ethylene oxide sterilization where color differential can be used to tell the ETO level which has been reached.

Table 4 illustrates the use of the indicator device to establish concentration levels of residual ETO reached during different time periods of aeration. Table 2 may be analyzed in the following manner depending on when the color of the exposed area matches that of the sealed area.

TABLE 2

| Liquid Crystal Formulation & Binder | Original (72° F.) | Color | | | | |
|---|---|---|---|---|---|---|
| | | Red | Green | Blue | Purple | Black |
| Ex. 1 | | | | | | |
| (b) | Red | <72° F. | <80° F. | <80° F. | 87° F. | 102° F. |
| (d) | Red | <72 | <80 | <80 | <80 | 98 |
| (i) | Black | 88 | 90 | 92 | 95 | 110 |
| Ex. 2 | | | | | | |
| (d) | Red | <72 | <80 | <80 | 84 | 96 |
| (h) | Black | <80 | <80 | <80 | 83 | 93 |
| Ex. 3 | | | | | | |
| (a) | Red-Green | <72 | <80 | <80 | <80 | 98 |
| (c) | Red | <72 | <80 | <80 | <80 | 96 |
| (e) | Green | <72 | <80 | <80 | <80 | 96 |
| (g) | Yellow-Bronze-green | <72 | <80 | <80 | <80 | 107 |
| | Green | <72 | <72 | <80 | <80 | 95 |
| Ex. 4 | | | | | | |
| (c) | Black | ~72 | <80 | 90 | 105 | 145 |
| (e) | Black | <80 | 84 | 92 | 104 | 150 |
| Ex. 5 | | | | | | |
| (b) | Brown-green | <72 | <72 | <80 | <80 | 90 |
| (f) | Yellow-green | <72 | <80 | <80 | <80 | 94 |
| Ex. 6 | | | | | | |
| (e) | Black | <80 | <80 | <80 | 80 | 94 |
| (f) | Black | <80 | <80 | <80 | 87 | 92 |

TABLE 3

Time of Ethylene Oxide Exposure (Sealed Area / Exposed Area)

| Formulation | Original Color | 15 Min. (140 ppm/ETO) | 30 Min. (220 ppm/ETO) | 1 Hr. (340 ppm/ETO) | 2 Hr. (460 ppm/ETO) | 4 Hr. (620 ppm/ETO) | 6 Hr. (1160 ppm/ETO) | 8 Hr. (1100 ppm/ETO) |
|---|---|---|---|---|---|---|---|---|
| Ex. 1 | | | | | | | | |
| (b) | Red | Sl. red / Blue | NC / NC | Red / NC | NC / Blue-purple | NC / Purple | NC / NC | NC / NC |
| (d) | Red | Red / Blue | NC / Purple | NC / NC | NC / Ft. Purple | NC / Black | NC / NC | NC / NC |
| (i) | Black | Green / Black | Blue-purple / NC | NC / NC | NC / NC | Blue / NC | NC / NC | NC / NC |
| Ex. 2 | | | | | | | | |
| (d) | Red | Red / Black | NC / NC | NC / NC | NC / NC | NC / NC | NC / NC | NC / NC |
| (h) | Black | Red / Blue | NC / Blue-purple | NC / Black | NC / NC | NC / NC | NC / NC | NC / NC |
| Ex. 3 | | | | | | | | |
| a | Red-green | Red / Purple | Green / NC | NC / Purple-black | NC / NC | Blue / NC | NC / NC | NC / NC |
| c | Red | Red / Blue-green | Green / Purple | NC / NC | NC / NC | NC / Purple-black | Blue-green / NC | NC / NC |
| e | Green | Red / Purple | Green / NC | NC / NC | NC / NC | NC / Purple-black | NC / NC | NC / NC |
| g | Yellow-bronze-Green Blue-purple | Red / Purple-black | Green / NC | NC / NC | NC / NC | NC / NC | NC / NC | NC / NC |
| i | Green | Red / Purple | NC / NC | Red-green / NC | NC / NC | NC / NC | Green / NC | NC / NC |

| Formulation | Original Color | 15 Min (160 ppm/ETO) | 30 Min. (300 ppm/ETO) | 1 Hr. (400 ppm/ETO) | 2 Hr. (640 ppm/ETO) | 4 Hr. (1000 ppm/ETO) | 8 Hr. (1500 ppm/ETO) | 24 Hr. (2880 ppm/ETO) |
|---|---|---|---|---|---|---|---|---|
| Ex. 4 | | | | | | | | |
| (c) | Black | Black / Red-brown | Red-brown / Green | Red / Blue-green | NC / NC | NC / Blue | NC / NC | Red-brown / NC |

TABLE 3-continued

| | \<15 Min.\> (160 ppm/ETO) | 30 Min. (260 ppm/ETO) | 1 Hr. (420 ppm/ETO) | 2 Hr. (560 ppm/ETO) | 4 Hr. (950 ppm/ETO) | 30 Hr. (4800 ppm/ETO) |
|---|---|---|---|---|---|---|
| (e) | Black / Red-green | NC / Green | NC / Blue-green | NC / Blue | NC / Dk. blue | Red-brown / NC |
| Ex. 5 | | | | | | |
| (b) | Green / Blue-purple | Blue / Purple | NC / Purple-black | NC / NC | NC / NC | NC / NC |
| (f) | Green / Blue-purple | Blue-green / Purple | Bronze-green / NC | NC / NC | NC / NC | NC / Dk. Purple |
| Ex. 6 | | | | | | |
| (e) | Blue / Dk. Blue | Red-blue / Purple | NC / Purple-black | Black / NC | NC / NC | NC / NC |
| (f) | Black / Blue | NC / NC | Blue / NC | Red-blue / NC | NC / Blue-purple | Ft. Blue / Purple |

Time of Ethylene Oxide Exposure (Sealed Area / Exposed Area)

TABLE 4

| | Time Aeration (Ambient 72° F.) (Sealed Area / Exposed Area) | | | |
|---|---|---|---|---|
| Formula | 24 Hrs. (800 ppm/ETO) | 48 Hrs. (400 ppm/ETO) | 72 Hrs. (360 ppm/ETO) | 144 Hrs. (280 ppm/ETO) |
| Ex. 1 | | | | |
| (b) | Red / Green | Tan / Tan | Ft. Red / Ft. Red | Sl. Rust / Sl. Rust |
| (d) | Red / Purple | Red / Red | NC / NC | NC / NC |
| (i) | Blue / Black | Green / Black | Red-green / NC | Black / Black |
| Ex. 2 | | | | |
| (d) | Red / Blue | Red / Ft. Red | NC / NC | NC / NC |
| (h) | Red / Blue-green | Red / Ft. Red | Ft. Red / Ft. Red | Black / Black |
| Ex. 3 | | | | |
| (a) | Green / Dk. Blue | Red-green / NC | Red-green / Blue | NC / Blue-green |
| (c) | Green / Blue | Green / Red-blue | Blue-green / Red | Blue / Red-Purple |
| (e) | Green / Blue | Rust / Rust | Olive-green / Olive-green | Ft. Rust / Ft. Rust |
| (g) | Green / Purple | Red / Red-blue | Red-green / Green-blue | Bronze-red / Bronze-red |
| (i) | Green / Blue-purple | Red / Red | Green / Green | Bronze-green / Bronze-green |

| Formula | 8 Hrs. (1540 ppm/ETO) | 24 Hrs. (1040 ppm/ETO) | 72 Hrs. (740 ppm/ETO) | 120 Hrs. (460 ppm/ETO) | 168 Hrs. (440 ppm/ETO) | 192 Hrs. (380 ppm/ETO) | 216 Hrs. (360 ppm/ETO) |
|---|---|---|---|---|---|---|---|
| Ex. 4 | | | | | | | |
| (c) | Blue-purple / Brown | Purple-brown / NC | NC / NC | NC / Dark Brown | Dark Brown / Dark Brown | NC / NC | NC / NC |
| (e) | Blue / Brown | Brown / Brown | NC / NC | Brown-black / Brown-black | NC / NC | NC / NC | NC / NC |
| Ex. 5 | | | | | | | |
| (b) | Blue-green / Red | NC / Bronze-red | Bronze-green / NC | NC / Yellow-green | NC / NC | NC / NC | NC / Bronze-green |
| (f) | Green / Red | NC / Bronze-red | NC / NC | NC / NC | NC / Yellow-green | Yellow-green / Yellow-green | NC / NC |

| | 8 Hrs. (2000 ppm/ETO) | 24 Hrs. (1600 ppm/ETO) | 96 Hrs. (480 ppm/ETO) | 120 Hrs. (460 ppm/ETO) | 168 Hrs. (400 ppm/ETO) |
|---|---|---|---|---|---|
| Ex. 6 | | | | | |
| (e) | Red-green / Blue | Green-blue / Ft. Blue | Black / Black | NC / NC | NC / NC |
| (f) | Ft. Blue / Black | Blue-purple / NC | Ft. Purple / Ft. Purple | NC / NC | NC / NC |

DETERMINATION OF RESIDUAL ETO BY COLOR DIFFERENCE

In addition to matching the color of the exposed vs sealed areas of the indicator device to determine safe residual ETO levels in the hospital devices, the difference in color between the exposed and sealed areas can be used to determine progress of aeration. The following is an example of how this technique works. A color scale is developed for use in monitoring the levels of ETO. A graph is prepared for each formulation used The level of ETO can be determined by using the number differences between the exposed and sealed areas and locating the position on the graph to determine the residual ETO. The following color scale key indicates how the method may be used.

| Color Scale | Number |
|---|---|
| Black | 0 |
| Dark Brown | 1 |
| Brown | 2 |
| Bronze | 3 |
| Brownish Green | 4 |
| Green | 5 |
| Bluish Green | 6 |
| Greenish Blue | 7 |
| Blue | 8 |
| Bluish Purple | 9 |
| Purple | 10 |
| Dark Purple | 11 |

A series of coatings were prepared using the formulations described in the following paragraphs.

| I | Example 1 | |
|---|---|---|
| II | Example 1 + 5% MBBA | |
| III | Cholesteryl nonanoate | 75% |
| | Cholesteryl chloride | 15% |
| | Cholesteryl oleyl carbonate | 10% |
| IV | III + 5% MBBA | |

Figure 4:
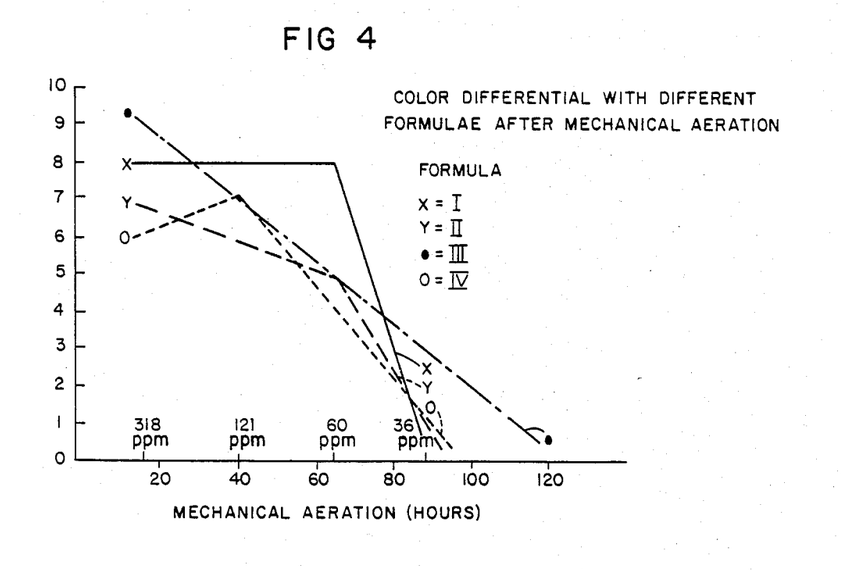
FIG. 4 is a graphic representation of the color differentials achieved with various useful formulae, according to the invention.

These formulations were dispersed in Acryloid B44 acrylic resin at a ratio of 1 part liquid crystal to 4 parts solid resin with 12 parts toluene as solvent. They were coated in the usual manner on black PVC to give a dry film thickness of 0.7-0.9 mil. These were covered with 3 mil clear plasticized polyvinyl chloride (PVC) to give the indicator shown in FIG. 1. These indicators were sterilized for three hours at 140° F. and then mechanically aerated. The graph (FIG. 4) gives the concentrations of ETO at numerical figures representing color difference between exposed and sealed areas. The level of residual ETO in ppm is also indicated on the graph.

PROTOTYPES FOR FIELD EVALUATION

It is necessary to identify and evaluate a number of significant factors before developing indicator device prototypes for actual field testing.

1. Aeration

The residual ethylene oxide (ETO) can be removed after sterilization, by a number of methods. The sterilized items may be stored on open shelves (natural) to allow the ETO to evaporate or diffuse into the surrounding atmosphere. This procedure requires an excessive period of time and also poses an environmental health hazard. Commercial mechanical aerators (mechanical) are available which use forced air at elevated temperatures (120° to 130° F.) to remove the ETO much faster. Hospitals use a combination of the natural and mechanical (hospital). Mechanical aeration is carried out for approximately 12 hours and the medical items are then removed, placed on shelves, and allowed to aerate naturally. Using 3 mil plasticized PVC to represent the worst case, the three above-described methods were compared and residual ETO was determined at different time intervals. Table 5 summarizes the findings.

TABLE 5

| Time (Hours) | 0 | 16 | 40 | 90 | 200 |
|---|---|---|---|---|---|
| Aeration Mode | | ETO Concentration (ppm) | | | |
| Mechanical | 1100 | 320 | 180 | 90 | 47 |
| Hospital | 1100 | 460 | 350 | 250 | |
| Natural | 1100 | 900 | 580 | 430 | |

In order to ensure a safe level of less than 250 ppm residual ETO in non-implants, mechanical treatment requires 30-40 hours, and the hospital process requires 90-100 hours. For a safe level of less than 25 ppm in implants, mechanical treatment requires 400-500 hours and hospital treatment about 2000 hours. The indicator devices gave results properly indicating ETO levels using each of the above processes.

2. Coating thickness

Bird applicators were used initially to apply the liquid crystal films at various thicknesses. It was generally found that color response varied due to non-uniformity of the applied coating. A doctor blade pilot coater was developed which applies very uniform coatings at the desired film thicknesses. A tower dryer was used to evaporate the solvent during coating operations. This equipment has been used to prepare the coated substrates for field evaluation. The film thickness of the liquid crystal film is critical. Very thin films are black and thicker films show no color difference between the exposed and covered areas during sterilization. Useful film thicknesses are between 0.3 and 1.5 mils with 0.4 mil to 0.9 mil being the preferred range.

3. Resin binders

The resin binders affect the performance of the indicator devices in a number of ways. A binder must be chosen which adheres properly to the substrate being used. Solvents in some binder systems will cause certain substrate films to curl. The effect on sensitivity and color play temperature has been shown in earlier examples. Compatibility of the resin with the liquid crystal formulation affects the clarity and color intensity or brightness of the indicator film. It should be understood that the choice of resin is experimentally determined and is dependent on the compositions of the indicator components. Particularly useful resins are the polymers and copolymers of acrylic esters, acrylonitrile, and vinyl esters.

4. Purity of liquid crystals and use of additives.

It has been mentioned earlier that since this is a comparative or differential indicator system, purity of coating compositions is compensated or "zeroed out" since the same film is used in both zones of comparison. Some liquid crystals were purified by recrystallization. There was no apparent difference in the brightness of the colors obtained from purified liquid crystal films when compared to the unpurified materials normally used. All materials evaluated have been obtained from commercial sources and none was chemically pure. The primary difference between the pure and technical liquid crystal products is the color play temperature, which depends on the mesomorphic range of the liquid crystal being used. Additives such as n-(p-methoxybenzylidene)-p-n-butylaniline (MBBA) and phenylazophenol cholesteryl carbonate were used to shift the color play range to lower temperatures and to improve resistance to degradation of the liquid crystals by light.

5. Structures

Structures other than shown in FIG. 1 can be used and still be within the scope of the invention. For example, instead of heat sealing the cover film 14 to the liquid crystal film 12 to form the annular zone 16, the two films may be joined by using a two-side pressure sensitive adhesive tape with the annular zone 16 cut out. A second liquid crystal coating of a composition the same as or differing from the composition of liquid crystal film 12 can be applied to the top surface of cover film 14. I have found that the sensitivity range can be changed and a more varied color response can be obtained by using such structures. The dimensions of the indicator device or the sizes or shapes of the annular zone 16 are not limited.

HOSPITAL FIELD EVALUATION

Trials were conducted at a Canadian general hospital using the following indicator systems

| 1 Indicator type comparable to FIG. 1 | |
|---|---|
| A. Liquid crystal Formulation: | |
| Cholesteryl nonanoate | 58.38% |
| Cholesteryl benzoate | 16.76% |
| Cholesteryl cinnamyl carbonate | 20.10% |
| Phenylazophenol cholesteryl carbonate | 4.76% |
| B. Coating Formulation: (parts by weight) | |
| Liquid crystal formulation (above) | 1 |
| Acryloid B44 resin | 4 |
| (acrylic ester from Rohm & Haas) | |
| Toluene | 12 |

The above coating was applied to black coated Fasson* micropore pressure sensitive tape at a dry film thickness of 0.7 mil. A clear 7.5 mil PVC film was heat-sealed to the liquid crystal/ resin layer. The adhesive backing of the indicator device was used to attach the indicator device to the medical device. Areas of the indicator which are not attached to the medical device are completely exposed to ethylene oxide during sterilization and the absorbed gas is rapidly lost during aeration. The color of the liquid crystal area sealed under the PVC cover and in contact with the medical device is dependent on the amount of ethylene oxide which penetrates through the medical device to the liquid crystal coating. During aeration, ethylene oxide is lost from the device and the color of the PVC covered liquid crystals reverts to the color of the exposed liquid crystal areas. The indicators prepared as described above were attached to a number of medical devices and evaluated. Sterilization conditions were 2.5 hours exposure at 120° F. followed by 12 hours of mechanical aeration. The colors of the indicators were noted after aeration periods, as shown in Table 6.

It would be very difficult for a color blind person to evaluate the above described indicators. This problem can be overcome by using a liquid crystal formulation which is sensitive to ethylene oxide (i.e., exhibits color change with ETO) but whose color play temperature range is above room temperature. Since the liquid crystal formulation does not exhibit color at room temperature, a symbol produced using this formulation appears invisible if attached to a black substrate. On exposure to ethylene oxide the letters or symbols would appear in some color which is dependent on the ethylene oxide concentration. With loss of ethylene oxide the symbol or letters would disappear on the black background.

A liquid crystal formulation whose color play range from black to brown through the visual spectrum to purple occurring in the temperature range 33° to 51° C. was used to coat a black substrate, Fasson micropore pressure sensitive adhesive tape. At temperatures below 33° C. the liquid crystal film was black. Circular 30 and triangular 32 shapes were cut from this liquid crystal film substrate and adhesively applied to a black PVC support 36. One of the shapes 30 was covered with 3 mil clear plasticized PVC 40 (a "worst case" material) while the second shape 32 was covered with 5 mil clear polyethylene 42 (representing those medical devices which do not retain ETO tenaciously). The covers 40 and 42 were sealed to the black PVC 36 to enclose the symbols 30 and 32. This is illustrated in FIG. 3. Initially, the entire indicator device appeared black. Sterilization exposure to ethylene oxide caused the liquid crystal coated shapes 30 and 32 to exhibit color. On aeration the shape 32 beneath the polyethylene 42 became black indicating medical relatively impervious devices such as scalpels, glass syringes, and other materials which do not retain ETO tenaciously were safe to use. The other symbol 30 remained colored and did not return to black until the loss of absorbed ETO in the clear PVC film 40 was at a safe level indicating that medical devices of the type which tenaciously retain ETO were safe to use. The shapes which appear different shades of gray to color blind people became invisible when the actual color returned to black.

The foregoing examples are merely illustrative to teach the products and the working of the present invention. Many other compositions which use different liquid crystals, resin binders, and which vary in the ratios of components were evaluated and further demonstrate the principles and the functioning of this invention. Based on the clear teaching of the invention others skilled in the art can also prepare still other working examples using components and methods not specifi-

TABLE 6

| | COLOR OF TAPE - TYPE INDICATORS | | |
|---|---|---|---|
| | Indicator Color (Exposed/Covered) | | |
| | Aeration | | |
| Sample | 12 Hours | 44 Hours | 162 Hours |
| 1. Indotrachael tube | green/green-blue | brown/brown-green | brown/green-brown |
| 2. Red rubber catheter | green-blue/blue | brown/green-blue | brown/green-brown |
| 3. Wooden tongue depressors | blue-green/blue-green* | brown/brown | |
| 4. Glass Syringe | blue-green/green-blue | brown/brown-green | brown/brown* |
| 5. Plastic airway | blue-green/green-blue | brown/brown* | |
| 6. Rubber anaesthesia mask | blue-green/blue-green* | brown/brown | |
| 7. Plastic trach tube | green-blue/blue | green-brown/green-blue | brown/brown-green |
| 8. Scalpel blades | blue-green/blue-green* | brown/brown | |
| 9. Telfa & gauze dressing | blue-green/blue-green* | brown/brown | |
| 10. Rubber anaesthesia tubing | blue-green/blue-green* | brown/brown | |

*Color match indicates little or no ethylene oxide remains in sample.

II Yes - no type indicators cally identified in the examples but described generally or effectively suggested in the specifications. For example, in the embodiment of FIG. 3, it would be feasible optionally to vary the roles of the shaped elements 30, 32 and the cover sheets 40, 42, and still achieve the aims of the invention—all without deviating from the inventive concepts taught herein. The resulting indicator devices would clearly fall within the scope of the invention, as defined in the appended claims.

What is claimed is:

1. An indicator assembly for providing a visual indication of relative concentrational levels of an alkylene oxide biocidal gas present in an article treated with such a biocidal gas, said assembly comprising a sheet-like supporting substrate, a film-like coating carried by said substrate, said coating including a liquid crystal composition responsive to biocidal gas reacting therewith to undergo color change, as a function of biocidal gas concentrations present, a transparent cover sheet overlying said coating, said cover sheet being permeable to permit transport of biocidal gas therethrough, means defining a viewable reference zone of said coating, said reference zone being covered by and sealed to said cover sheet and separated thereby from an ambient system, said reference zone being distinct from a visible comparison area of said coating, and said comparison area being covered by said cover sheet in a non-isolating manner to be directly exposed to the same ambient system.

2. The indicator device as set forth in claim 1 wherein said liquid crystal composition includes a mixture of three types of cholesteric liquid crystals, said mixture comprising about 30% to about 80% by weight of a cholesteryl ester of fatty acid having from 6 to 20 carbon atoms, from about 5% to about 40% by weight of a member selected from the group consisting of cholesteryl oleyl carbonate and cholesteryl 2-(2-alkoxyethoxy) ethyl carbonates in which the alkoxy group has from 1 to 4 carbon atoms, and mixtures thereof, and from about 0.5% to about 40% by weight of a member selected from the group consisting of cholesteryl benzoate, cholesteryl cinnamate, cholesteryl furfuryl carbonate, cholesteryl allyl carbonate, cholesteryl bromide, cholesteryl nitrate, cholesteryl cinnamyl carbonate, cholesteryl methallyl carbonate, and mixtures thereof.

3. The indicator device as set forth in claim 1 wherein said liquid crystal composition comprises from about 30% to about 80% by weight of a cholesteryl ester of a fatty acid having from 6 to 20 carbon atoms, and from about 0.5% to about 40% by weight of a member selected from the group consisting cholesteryl benzoate, cholesteryl cinnamate, cholesteryl furfuryl carbonate, cholesteryl allyl carbonate, cholesteryl bromide, cholesteryl nitrate, cholesteryl cinnamyl carbonate, cholesteryl methallyl carbonate, and mixtures thereof.

4. The indicator device as set forth in claim 1 wherein said liquid crystal composition includes a cholesteric liquid crystal, a binder as a constituent of said coating carried by said substrate, a solvent for said binder chemically inert to said binder and removable by evaporation at a temperature below about 250° F.; whereby evaporation of said solvent provides a dispersion in which said binder is in a continuous phase and said liquid crystal is in a dispersed phase.

5. The indicator device as set forth in claim 4 wherein said solvent is water and wherein said liquid crystal is dispersed as droplets throughout a mass of solid binder.

6. The indicator device as set forth in claim 4 wherein said solvent is a solvent also for said cholesteric liquid crystal, whereby evaporation of said solvent yields a single solid phase system.

7. The method of fabricating an indicating device for providing a visual representation of relative concentrational levels of an alkylene oxide biocidal gas present in an article treated with such a biocidal gas, said method comprising the steps of preparing a cholesteric liquid crystal, coating composition, applying said coating composition as a fluid film on a supporting substrate, evaporating said solvent from said substrate at a temperature below about 250° F. to provide a coating bonded to said substrate, superimposing on at least a portion of said coating transparent cover sheet permeable to the biocidal gas and having a thickness correlated with an effective thickness of an article to be permeated by the biocidal gas, bonding said cover sheet to said coating to define a reference zone and a comparison area of said coating, said reference zone being in biocidal gas flow communication with an ambient system through said cover sheet, said comparison area being in direct communication with the ambient system and said reference zone and said comparison area being viewable through said cover sheet superimposed thereon.

8. An indicator assembly for providing a visual indicator having two different visually discernible degrees of sensitivity to alkylene oxide biocidal gas in effecting color change as a function of concentrations of alkylene oxide biocidal gas present, said assembly comprising a base substrate, a film-like coating applied to said substrate, said coating including a liquid crystal component responsive to biocidal gas reacting therewith to undergo and to exhibit color change as a function of concentration of biocidal gas present, first and second laterally spaced demarked areal zones of said coating exhibiting visual distinguishable marginal contours, first and second cover sheets overlying respective said first and second zones and sealed to said film-like coating, said first and second cover sheets being characterized in that they exhibit different degrees of permeability to biocidal gas upon exposure thereto, said zones undergoing color changes at different rates upon exposure of said zones to biocidal gas and upon removal of biocidal gas from said zones.

9. The method for indicating the amount of residual alkylene oxide present in an alkylene oxide treated article by using a gas indicating device having a gas-sensitive cholesteric liquid crystal composition applied as a coating on a supporting substrate, a mechanically isolated zone of said coating being sealed from direct exposure to an ambient system, and a transparent, gas-permeable cover sheet covering said isolated zone of said coating, and said zone being viewable through said cover sheet, said method comprising the steps of exposing said indicating device to an alkylene oxide biocidal gas, diffusing a biocidal gas through said cover sheet to contact said zone of said coating, visually noting any color change occurring in said zone, aerating said indicating device, and again visually noting any color change in said zone of said coating and comparing the color of said zone with that of an area exposed directly to the ambient system, the steps of said method being carried out in the presence of an article whereby the gas indicating device and the article are simultaneously exposed to said steps.

* * * * *